United States Patent
Patchev et al.

(12) United States Patent
(10) Patent No.: US 6,670,493 B2
(45) Date of Patent: Dec. 30, 2003

(54) METHODS AND COMPOSITIONS FOR TREATING DISEASES DUE TO ANDROGEN DEFICIENCY WITH GLUCOCORTICOID RECEPTOR ANTAGONIST COMPOUNDS AND NEW COMPOUNDS

(75) Inventors: Vladimir Patchev, Jena (DE); Lothar Sobek, Jena (DE); Gerd Schubert, Jena (DE)

(73) Assignee: Jenapharm GmbH & Co. KG, Jena (DE)

( * ) Notice: Subject to any disclaimer, the term of this patent is extended or adjusted under 35 U.S.C. 154(b) by 0 days.

(21) Appl. No.: 10/218,085

(22) Filed: Aug. 13, 2002

(65) Prior Publication Data

US 2003/0064973 A1 Apr. 3, 2003

Related U.S. Application Data

(60) Provisional application No. 60/315,099, filed on Aug. 27, 2001.

(30) Foreign Application Priority Data

Aug. 16, 2001 (DE) .......................................... 101 40 113

(51) Int. Cl.$^7$ ............................. C07J 1/00; A61K 31/56
(52) U.S. Cl. ........................ 552/648; 514/177; 514/179
(58) Field of Search ......................... 552/648; 514/177, 514/179

(56) References Cited

U.S. PATENT DOCUMENTS 5,693,628 A * 12/1997 Schubert et al. ............ 514/179
6,512,130 B1 * 1/2003 Hazra et al. ................ 552/648

FOREIGN PATENT DOCUMENTS

| EP | 0 057 115 A2 | 8/1982 |
|----|--------------|--------|
| EP | 0 683 172 A1 | 11/1995 |
| EP | 0 763 541 A1 | 3/1997 |
| WO | 99/63976 | 12/1999 |
| WO | 01/44267 A1 | 6/2001 |

* cited by examiner

Primary Examiner—Shailendra Kumar
(74) Attorney, Agent, or Firm—Michael J. Striker

(57) ABSTRACT

The method of treating or preventing a disease in a human male or a male animal caused by a decreased production of androgens, such as testosterone, in the human male or male animal includes administering an effective amount of a glucocorticoid receptor antagonist to the human male or the male animal in order to increase production of the androgens. These diseases include male sexual dysfunction, infertility and hypogonadism. Novel androgen receptor antagonist compounds and methods of synthesis are also described.

16 Claims, No Drawings

METHODS AND COMPOSITIONS FOR TREATING DISEASES DUE TO ANDROGEN DEFICIENCY WITH GLUCOCORTICOID RECEPTOR ANTAGONIST COMPOUNDS AND NEW COMPOUNDS

CROSS-REFERENCE

The subject matter disclosed herein is at least partially the same as the subject matter disclosed in U.S. Provisional Application, Ser. No. 60/315,099, filed Aug. 27, 2001.

BACKGROUND OF THE INVENTION

The invention relates to the use of glucocorticoid receptor antagonists for the prevention and treatment of diseases of the male reproductive system, as well as to glucocorticoid receptor antagonists, which are particularly suitable for this purpose.

It is well known that physical and/or mental stress, age as well as exogenous factors, such as drugs and excessive consumption of alcohol, can lead to sexual dysfunctions and hypogonadism in men. According to presently existing understanding, these diseases are caused by a decreased androgen production, especially by a decreased testosterone production.

Various attempts were made to treat the above diseases. However, the drugs used either were not sufficiently effective or showed serious side effects, which harmed the patients more than they healed them or were not suitable for other reasons.

There is therefore an appreciable demand for new compounds to prevent and/or treat the diseases above.

SUMMARY OF THE INVENTION

It is therefore an object of the present invention to be able to prevent and treat the symptoms, caused by a decreased androgen production. It is furthermore an object of the present invention to make available compounds, which can be used advantageously for the treatment and/or prevention of diseases, which are caused by a decreased androgen production.

Pursuant to the invention, the aforementioned objective is accomplished by the use of glucocorticoid receptor antagonists. Within the meaning of the present invention, glucocorticoid receptor antagonists are understood to be drugs, which inhibit the action of glucocorticoids by binding to glucocorticoid receptors.

The present invention is based on the surprising realization that, when glucocorticoid receptor antagonists are administered, the androgen production, which previously was decreased by the excess of glucocorticoid, is increased.

If for example Leydig cells (cells from the testes, which produce male sex hormones) are stimulated with human chorion gonadotropin (hCG), there is an increase in testosterone production due to these cells. If now the cells are incubated with hCG and a glucocorticoid, such as dexamethasone (a ligand for the glucocorticoid receptor (GR)), a significant decrease in testosterone production can be observed. It has now been found that the decrease in testosterone production is prevented by the glucocorticoid, if the latter is administered together with a glucocorticoid receptor antagonists in such an experiment. This effect was observed not only in cells, but also in experimental animals.

In experimental animals, stress or an increased glucocorticoid blood level cause an inhibition of the secretory activity of the endocrine system of the male gonads, which is documented by a decreased serum testosterone level. At the same time, an inhibition of (decrease in) male sexual activity is observed. These symptoms are characteristic, for instance, of hypogonadism and are observed in other syndromes, such as stress and, in particular, chronic stress.

Glucocorticoid receptor antagonists, which may be natural or synthetic compounds, occupy the glucocorticoid receptor and, in doing so, displace the natural (endogenous) ligand of the glucocorticoid receptor, the glucocorticoids, so that, by a selective antagonization of the glucocorticoid receptor, the transfer of chemical signals over this receptor, at the very least, is reduced, but may even also be prevented almost completely. By the displacement of the glucocorticoids by glucocorticoid receptor antagonists, the excessive occupation of glucocorticoid receptors by glucocorticoids is antagonized.

This reduction in or prevention of the occupation of the glucocorticoid receptors by glucocorticoids may be desirable especially if the glucocorticoid level in the body is increased. Such an increase can be caused, for example, by (i) physical or mental stress, (ii) a pathological increase in the secretory activity of the adrenal cortex, (iii) alcohol and drug misuse and withdrawal, (iv) exogenous administration of medicinal drugs, such as cortisol, for the treatment of chronic diseases and (v) aging.

If the realizations and experimental results, described above, are combined, they lead to the assumption, without being definitive, that the excessive secretion of glucocorticoids results in an excessive occupation of glucocorticoid receptors in endocrine cells of the male gonad and/or in the relevant regions of the central nervous system. This can cause disorders of the male reproductive system due to a decrease in the production of male sex hormones (androgens, especially testosterone), an impairment of the responsiveness of the endocrine system of the male gonads for the stimulating effect of gonadotropin, an impairment of the neuronal responsiveness to sexual stimuli and, consequently, an erectile dysfunction. These symptoms are described generally by the expression "hypogonadism in males", which includes a plurality of somatic and endocrine dysfunctions. In the sense of the present invention, "hypogonadism" does not include the consequences of the surgical removal (gonadectomy) or of the congenital defects (agenesia) of the male gonads.

Especially the hypogonadism in males, especially the hypogonadotropic hypogonadism, sexual dysfunctions in males and infertility can be treated and/or prevented particularly well by administering glucocorticoid receptor antagonists, the excessive occupation of the glucocorticoid receptors by glucocorticoid receptor antagonists in the organism, especially in the organs responsible for reproduction and/or in neuronal circuits, which are responsible for its control, being reduced or prevented.

There are two mechanisms, by means of which the interaction between glucocorticoids and glucocorticoid receptors can proceed. The type 1 mechanism is distinguished by an interaction between the glucocorticoid receptor and special DNA sequences. On the other hand, the interaction between glucocorticoid receptors and other transcription factors, in the absence of specific DNA binding, participates possibly over a direct protein—protein intraction in the type 2 mechanism.

In a preferred embodiment, the glucocorticoid receptor antagonist, which is used pursuant to the invention, antagonizes the type I transcription induction of the glucocorticoid receptor gene. A particularly good therapeutic effect is noted in the treatment of the aforementioned diseases when glucocorticoid receptor antagonists are used. It is well known that glucocorticoid play an important role in the immune system. Since the glucocorticoid-induced immune suppression takes place exclusively by the type 2 mechanism of the glucocorticoid receptor action, glucocorticoid receptor antagonists are preferred, which antagonize the type 1 transcription induction of the glucocorticoid receptor gene, since by these means no negative effects on the immune system can be detected.

In a preferred embodiment, the glucocorticoid receptor essentially does not antagonize the type 2 transcription inhibition. When glucocorticoid receptor antagonists with this property were used pursuant to the invention, it was not possible to detect any side effects, especially side effects on the immune system. In this connection, the expression "essentially does not antagonize" means that possible antagonizing can be detected only insofar as non-physiological or pathological effects were not observed.

Preferably, the glucocorticoid receptor antagonist employed for the inventive use, essentially do not bind to other steroid receptors. In this connection, the expression "essentially do not bind" means that only sufficient glucocorticoid receptor antagonist binds to other steroid receptors as glucocorticoid receptors, so that no effects, brought about by the other receptors, can be noted or existing physiological effects are eliminated. Examples of other steroid receptors are the mineral corticoid receptors, estrogen, progesterone receptors and androgen receptors. Due to this high selectivity of the glucocorticoid receptor antagonists, which are used pursuant to the invention, the effects desired pursuant to the invention, are particularly clearly pronounced and, with that, the diseases which are to be treated pursuant to the invention, can be treated particularly well. On the other hand, undesirable side effects, especially those caused by an occupation of other glucocorticoid receptors, are not observed.

Preferably, the signals, transferred by glucocorticoid receptors are not inhibited completely by the glucocorticoid receptor antagonists, which are used pursuant to the invention. In this connection, it should be pointed out that, for maintaining basic vital functions and for an adequate adaptation to challenges brought about by the environment, a certain level of signals, transmitted by glucocorticoid receptors, is necessary. For these reasons, a complete inhibition of signals, transferred by glucocorticoid receptors, is not desirable, especially in order to prevent undesirable effects of the interruption of the feedback, brought about by glucocorticoids (that is, iatrogenic glucocorticoid receptor resistance) and an uncontrolled pituitary-adrenal hyperactivity.

For the inventive use, the glucocorticoid receptor antagonists can be administered enterally and parenterally, for man especially in a dose of 0.0001 to 100 mg per kg of body weight. The glucocorticoid receptor antagonist can be administered together with pharmaceutically suitable adjuvants. The glucocorticoid receptor antagonists can be pressed into a solid-dose unit, such as a tablet or be present in some way, such as capsules or suppositories. By using pharmaceutically compatible liquids, the glucocorticoid receptor antagonists can also be prepared in the form of solutions, suspensions, emulsions, as injection preparations, droplets or sprays. Medicinal drugs for the inventive use furthermore may contain additives, such as fillers, dyes and polymeric binders. Basically, any pharmaceutically compatible additive can be used, which does not interfere negatively with the function of the glucocorticoid receptor used pursuant to the invention. Suitable carriers, with which the glucocorticoid receptor antagonists can be administered, comprise lactose, starch cellulose derivatives and mixtures thereof.

Glucocorticoid receptor antagonists may be compounds, which are known. In the case of unknown compounds, it is possible to carry out simple tests, which are known to those skilled in the art, to establish whether these compounds have the properties of a glucocorticoid receptor antagonist. For this purpose, for example, a compound, which is to be tested, is incubated together with a glucocorticoid in a test system for glucocorticoid receptors and tested to establish whether the effect, brought about by the glucocorticoids, is reduced in the presence of the antagonist in this test system.

Glucocorticoid receptor antagonists are, for example the 11,21-bisphenyl-19-norpregnane derivatives, which are described, for example, in the EP 683 172 A1 and have the formula

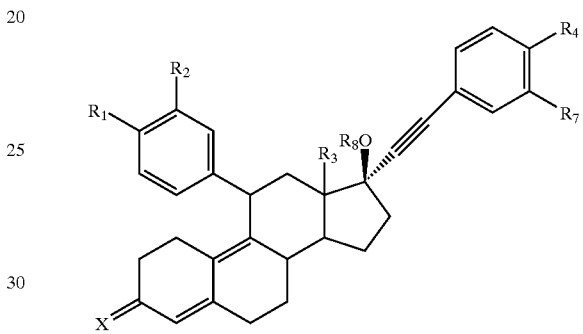

in which $R_1$ represents hydrogen, halogen, (1–6C) alkoxy and $NR_5R_6$, $R_5$ and $R_6$ being selected independently of one another from hydrogen, and (1–6C) alkyl or $R_5$ and $R_6$ together forming a (3–6C) alkylene, $R_2$ represents hydrogen, or $R_1$ and $R_2$ together form a (1–3C) alkylenedioxy group, which optionally is substituted with one or more halogen atoms, $R_3$ represents methyl or ethyl, $R_4$ is selected from C(O)—$NR_5R_6$, $SO_n$-(1–6C) alkyl, which optionally is substituted by one or more halogen atoms, or $SO_n$-(3–6C) cycloalkyl, n being 1 or 2, $SO_2$–$NR_5R_6$,2-oxypyrrolidinyl and $NR_5R_6$, $R_7$ represents hydrogen or (1–6C) alkyl, $R_8$ represents hydrogen or a carboxy-1-oxo(1–6C) alkyl and X is selected from (H, OH), O, and NOH. These are particularly suitable for the inventive use, because the appropriate diseases can be treated particularly well.

Other glucocorticoid receptor antagonists, also suitable for the inventive use because the aforementioned diseases can be treated well, are the 11-(phenyl substituted)-estra-4, 9-diene derivatives described in the EP 0 763 541 A1 and having the formula

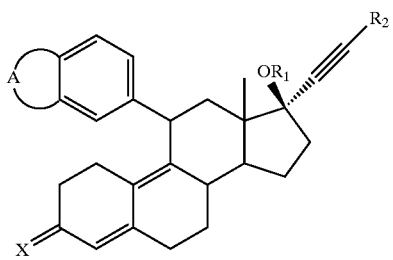

in which A represents a 5- or 6-membered ring with two hetero atoms, which are not linked to one another and are selected independently from O and S, the ring optionally being substituted by one or more halogen atoms, or A represents a 5- or 6-membered ring, which does not have any carbon-to-carbon double bonds and contains one hetero atom, which is selected from O and S, the hetero atom being linked to a phenyl group at the position marked with a star, the ring optionally being substituted by one or more hydrogen atoms, $R_1$ representing hydrogen or 1-oxo(1–4C) alkyl, $R_2$ representing hydrogen, (1–8C) alkyl, halogen or $CF_3$, X being selected from (H, OH,) O and NOH and the dashed line representing an optionally present bond.

Other glucocorticoid receptor antagonists, like those described in WO 01/44267, can be found among compounds represented by the following formula

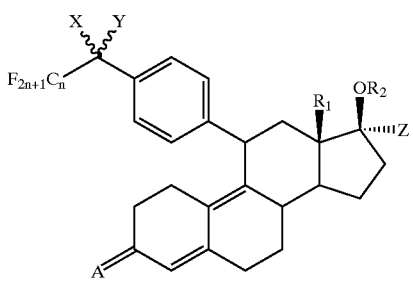

in which $R_1$ represents a $C_{1-6}$ alkyl group, $R_2$ is a hydrogen atom, a $C_{1-6}$ alkyl group or a $C_{1-6}$ acyl group, X is a hydroxyl group or a trimethylsiloxy group and Y is a hydrogen atom or a perfluoroalkyl group of the general formula $C_nF_{2n+1}$, or X and Y together represent an oxo group or an oximino group $NOR_3$, Z represents a hydrogen atom, a $C_{1-6}$ alkyl group or a substituted methylene group $CH_2W$, in which W represents a hydroxyl group, a $C_{1-6}$ alkoxy group, a $C_{1-6}$ alkylthio group, a halogen atom or pseudohalogen, and A represents an oxo group, an oximino group $NOR_3$, a 1,3-dithian group or a 1,3-dithiolan group, $R_3$ being a hydrogen atom, a $C_{1-8}$ alkyl, aryl, alkylaryl or arylalkyl group, or a $C_{1-8}$ acyl group, a $CONHR_4$, $COSR_4$ or $COOR_4$ group, $R_4$ being a hydrogen atom or a $C_{1-8}$ alkyl, aryl, alkylaryl or arylalkyl group and n a whole number from 1 to 4.

As glucocorticoid receptor antagonists, the compounds RU38486 (EP 0057 115) and KB 285 (WO 99/63976) of the two following structural formulas also come into consideration:

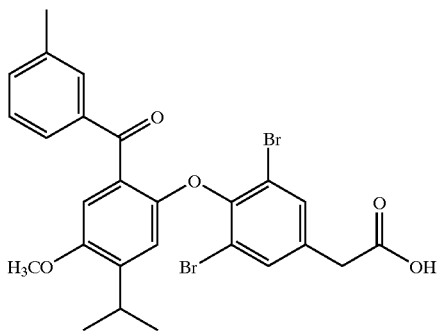

KB 285

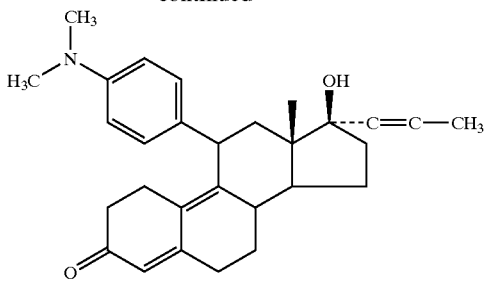

RU38486

As glucocorticoid receptor antagonists, the compounds, which are given in the following formula and are also an object of the present invention, are particularly suitable because of their especially good effect when used for the treatment of the diseases named above:

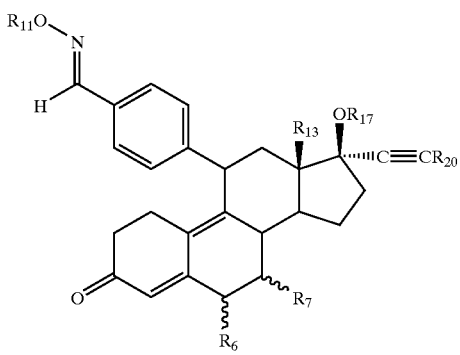

wherein $R_6$ is a hydrogen atom or a halogen atom, such as fluorine, chlorine or bromine, in the α or β position, or a $C_{1-6}$ alkyl group in the α or β position, $R_7$, independently of $R_6$, is a hydrogen atom or a halogen atom, such as fluorine, chlorine or bromine, in the α or β position, or a $C_{1-6}$ alkyl group in the α or β position, $R_{11}$ is a hydrogen atom, a $C_{1-6}$ alkyl group, a $C_{1-6}$ acyl group, a $CONHR_{21}$, $COSR_{22}$, or $COOR_{22}$ group, $R_{21}$ being a $C_{1-6}$ alkyl group or a substituted or not substituted $C_6$–$C_{10}$ aryl group and $R_{22}$ a $C_{1-6}$ alkyl group or a substituted or not substituted $C_{6-10}$ aryl group, $R_{13}$ is a methyl or ethyl group, $R_{17}$ is a hydrogen atom or a $C_{1-6}$ alkyl group $C_{1-6}$ acyl group and $R_{20}$ is a hydrogen atom, a $C_{16}$ alkyl group or a substituted or not substituted $C_{6-12}$ aryl group.

Examples of aryl groups are phenyl to naphthyl groups. These may have one or more substituents, which are selected independently of one another. The substituents may be in the o-, m- or p-position. Examples of substituents are linear or branched $C_1$–$C_6$ alkyl groups, such as methyl, ethyl, propyl or isopropyl, halogens, such as chlorine or bromine, and pseudohalogens, such as azide or rhodonide groups. The substituents of the aryl groups, particularly in the case of $R_{20}$, furthermore may be substituted phenyl groups, selected from sulfonamides of the type $C_6H_4SO_2NR_{21}R_{22}$, sulfonalkyls of the type $C_6H_4SO_2R_{23}$, aminosulfones of the type $C_6H_4NHSO_2R_{23}$ or hydroxysulfonealkyls of the type $C_6H_4OSO_2R_{24}$ in which $R_{21}$ to $R_{24}$ are linear or branched $C_1$–$C_6$ alkyls, such as methyl, ethyl, propyl or isopropyl.

Because of their particularly positive properties in treating the aforementioned diseases, preferred representatives of the inventive compounds are:

4-(17α-ethinyl-17β-hydroxy-3-oxoestra-4,9-diene-11β-yl)benzaldehyde-1(E)-oxime, 4-(17α-ethinyl-17β-methoxy-3-oxoestra-4,9-diene-11β-yl)benzaldehyde-1(E)-oxime, 4-(17β-hydroxy-17α-propinyl-³-oxoestra-4,9-diene-11β-yl)benzaldehyde-1(E)-oxime, 4-(17β-methoxy-17α-propinyl-³-oxoestra-4,9-diene-11β-yl)benzaldehyde-1(E)-oxime, 4-[17β-hydroxy-17α,21-(phenyl)19nor-3-oxopregna-4,9-diene-20-yn-11β-yl]-benzaldehyde-1(E)-oxime, 4-[17β-hydroxy-17α,21-(4'-methylphenyl)19-nor-3-oxopregna-4,9-diene-20-yn-11β-yl]-benzaldehyde-1(E)-oxime, 4-[17β-hydroxy-17α,21-(t-butyl)19-nor-3-oxopregna-4,9-diene-20-yn-11β-yl]-benzaldehyde-1(E)-oxime, 4-[17β-hydroxy-17α,21-(4'-t-butylphenyl)19-nor-3-oxopregna-4,9-diene-20-yn-11β-yl]-benzaldehyde-1(E)-oxime, 4-[17β-hydroxy-17α,21-(4'-methylsulfonylphenyl)19-nor-3-oxopregna-4,9-diene-20-yn-11β-yl]-benzaldehyde-1(E)-oxime, 4-[17β-hydroxy-17α,21-(4'-methylsulfonylphenyl)19-nor-3-oxopregna-4,9-diene-20-yn-11β-yl]-benzaldehyde-1(E)-[N-(ethylamine)carbonyl]oxime, 4-[17β-hydroxy-17α,21-(4'-methylsulfonylphenyl)19-nor-3-oxopregna-4,9-diene-20-yn-11β-yl]-benzaldehyde-1(E)-[S-(ethylthio)carbonyl]oxime, 4-[17β-hydroxy-17α,21-(4'-methylsulfonylphenyl)19-nor-3-oxopregna-4,9-diene-20-yn-11β-yl]-benzaldehyde-1(E)-[O-(ethyloxy)carbonyl]oxime, 4-[17β-hydroxy-17α-propinyl-13β-ethyl-3-oxoestra-4,9-diene-11β-yl]-benzaldehyde-1(E)-oxime, 4-[6β-chloro-17β-hydroxy-17α-propinyl-3-oxoestra-4,9-diene-11β-yl]-benzaldehyde-1(E)-oxime, 4-[7α-methyl-17β-hydroxy-17α-propinyl-3-oxoestra-4,9-diene-11β-yl]-benzaldehyde-1(E)-oxime, 4-[17β-acetoxy-17α-propinyl-3-oxoestra-4,9-diene-11β-yl]-benzaldehyde-1(E)-oxime, 4-[17β-acetoxy-17α,21-(4'-methylsulfonylphenyl)19-nor-3-oxopregna-4,9-diene-20-yn-11β-yl]-benzaldehyde-1(E)-O-acetyloxime, 4-[17β-hydroxy-17α-propinyl-3-oxoestra-4,9-diene-11β-yl]-benzaldehyde-1(E)-[N-trifluoromethoxy-phenylamino)carbonyl]oxime.

The above compounds are particularly suitable for treating and/or preventing diseases, brought about by an androgen deficiency.

The present invention furthermore relates to a method for the synthesis of the inventive compounds, for which 11β-formylphenylsteroids of the general formula

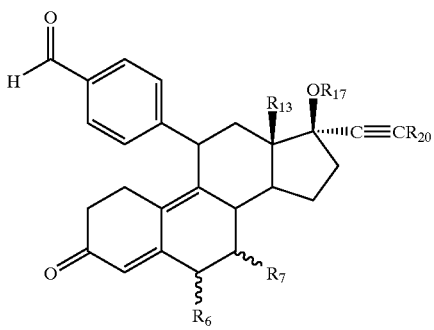

are reacted with hydroxylamine, salts of hydroxylamine, such hydroxylamine hydrochloride or hydroxylamine hydrogen sulfate, in solvents, such as pyridine, dimethylformamide or alcohols, in the presence of bases, such as alkali or alkaline earth carbonates or hydroxides, or potassium t-butanolate, to the corresponding 11 β-benzaldoximes of the aforementioned formula and the hydroxyl groups optionally are etherified, esterified or converted into urethane groups.

With this inventive method, it is possible, in a particularly simple, fast and inexpensive manner, to synthesize the inventive compounds in a highly pure form and in high yields.

EXAMPLES

The following examples explain the invention, however, without limiting it.

Example 1

Increasing the Testosterone Production by Glucocorticoid Receptor Antagonists in Leydig Cells Description of the Method Testicular cells were prepared from the testicles of sexually mature, 12-week old, male Wistar rats by means of a collagenase treatment. Leydig cells were obtained from this preparation by a continuous Percoll gradient centrifugation.

Freshly prepared Leydig cells were sown in microtiter plates in 100 µL of DMEM/F12 with phenol red (20,000) cells/well) with addition of 0.1% BSA, penicillin (100 U/ml) and streptomycin (100 µg/ml). After one hour, the medium was changed with addition of substance. For 18 hours, the Leydig cells were incubated with dexamethasone alone or together with glucocorticoid receptor antagonists (250 µL of DMEM/well with addition of penicillin (100 U/ml) and streptomycin (100 µg/ml)). The DMEM medium did not contain any phenol red. After that, the medium was changed once more and the testosterone production of the cells was stimulated with human chorionic gonadotropin (hCG, Sigma, 0.5 ng/ml) for 8 hours in the presence of dexamethasone or the glucocorticoid receptor antagonist. Ethanol was used as solvent for dexamethasone and the glucocorticoid receptor antagonists; the final concentration of the ethanol was not more than 0.2%.

Aliquots of the supernatant were frozen at −70° C. Testosterone was measured with a commercial Elisa (IBL, Hamburg). The standard curve of testosterone Elisa was then adapted to the cell culture conditions.

Parallel to the testosterone measurement, cell damage was determined after the 26 hours by measuring the activity of the mitochondrial succinate dehydrogenase (WST-1 test, B öhringer, Mannheim).

The results are given in the following Table.

Results

The stimulation of cultured Leydig cells with hCG results in a multiple increase in the testosterone production. The treatment of Leydig cells with dexamethasone in a concentration of $10^{-7}$ M led to a significant decrease in the hCG-induced testosterone production in vitro. Simultaneous use of glucocorticoid receptor antagonists in a dose of $10^{-6}$ M completely prevents the inhibition of testosterone production by dexamethasone (Table 1).

The activity of the mitochondrial succinate dehydrogenase in cultured Leydig cells is not changed by a stimulation with hCG in the given dose. Treatment of the cells with dexamethasone in a dose of $10^{-7}$ M leads to a significant inhibition of the mitochondrial activity; the latter is eliminated completely by the simultaneous administration of a glucocorticoid receptor antagonist in a concentration of $10^{-6}$ M (Table 2).

Conclusions

The activation of the glucocorticoid receptor in Leydig cells results in a significant decrease in the endocrine secretory activity (demonstrated by a reduced testosterone production after hCG stimulation) as well as in clear symptoms of cell damage (indicated by a decreased activity of the mitochondrial succinate dehydrogenase). A treatment with antagonists of the GR prevents the occurrence of these symptoms, which are characteristic of morphological and functional damage and largely define the state of hypogonadism.

Table 1

Testosterone production by primary rat Leydig cells after treatment with 100 nM of dexamethasone (DEX) alone or with additional administration of glucocorticoid receptor antagonists (1 μm). The data represents average values ± standard deviations (SD) from 6 to 12 parallel determinations; stars indicate that the differences from experimental conditions with hCG alone are significant.

TABLE 1

| | Testosterone Production (ng/ml) | | |
|---|---|---|---|
| Experimental Conditions | Average value ± SD (ng/ml) | n | Average value ± SD (%) |
| Basal | 0.17 ± 0.03 | 6 | 0.00 ± 0.63 |
| hCG alone (0.5 ng/ml) | 4.26 ± 1.11 | 12 | 100.00 ± 27.25 |
| hCG (0.5 ng/ml) + DEX | 2.00 ± 0.58P | 12 | 44.63 ± 14.08P |
| hCG + DEX + RU38486 | 4.48 ± 1.14 | 6 | 105.23 ± 27.83 |
| hCG + DEX + GRA1 | 3.57 ± 0.83 | 6 | 83.00 ± 20.40 |
| hCG + DEX + GRA2 | 3.48 ± 0.64 | 6 | 80.97 ± 15.47 |
| hCG + DEX + GRA3 | 4.52 ± 1.01 | 6 | 106.30 ± 24.75 |

RU 38 486=11β-dimethylaminophenyl-17β-hydroxy-17α-propinyl-estra-4,9-diene-3-one GRA 1=4-(17β-methoxy-17α-(methoxymethyl)-estra-4,9-diene-3-one-11β-yl]2,2,2-trifluoroacetophenone-1 (Z)-oxime GRA 2=11-(5-(1,3-benzodioxol)-17α,21-[(4'-methylsulfonyl)phenyl]17β-hydroxy-19-norpregna-4,9-diene-20-yn-3-one GRA 3=4-[17β-hydroxy-17α,21-(4'-methylsulfonylphenyl)-19-nor-3-oxopregna-4,9-diene-20-yn-11β-yl]benzaldehyde-1(E)-oxime

TABLE 2

Activity of the mitochondrial succinaldehyde dehydrogenase in primary rat Leydig cell cultures after treatment with 100 nM of dexamethasone (DEX) alone or with additional administration of glucocorticoid receptor antagonists (1 μm). The data represents average values ± standard deviations (SD) from 5 to 12 parallel determinations; stars indicate that the differences from experimental conditions with hCG alone are significant.

| | Succinate Dehydrogenase Activity (Absorptions Units) | |
|---|---|---|
| Experimental Conditions | Average value ± SD | n |
| Basal | 0.269 ± 0.020 | 6 |
| hCG alone (0.5 ng/ml) | 0.281 ± 0.041 | 12 |
| hCG (0.5 ng/ml) + DEX | 0.192 ± 0.036* | 12 |
| hCG + DEX + RU38486 | 0.311 ± 0.031 | 6 |
| hCG + DEX + GRA1 | 0.289 ± 0.040 | 5 |
| hCG + DEX + GRA2 | 0.363 ± 0.032 | 6 |
| hCG + DEX + GRA3 | 0.313 ± 0.018 | 6 |

Example 2

Increased Testosterone Production as a Result of Administering Glucocorticoid Receptor Antagonists to Rats Description of the Method Sexually mature, 3-month old male rats of the CD breeding line (Charles River GmbH, Sulzfeld, Germany) were kept in groups of 4 animals under controlled illumination (light:darkness 12:12 hours) with free access to food and drinking water. After a 1-week adaptation, the animals were tested by exposure to ovarectomized, estrogen-treated females for the presence of male sexual behavior (G. Dörner, Hormones and brain differentiation, Elsevier, Amsterdam, 1976, pp. 126–132). Only males, who showed a robust, positive behavior (more than 5 complete copulations within a period of observation of 5 minutes) on three consecutive days, were included in the testing. The animals of the reference group received intraperitoneal injections of dexamethasone (Fortecortin: Merck, Darmstadt, Germany) daily according to the following schedule: 0.5 mg/kg on days 1 to 3, 1 mg/kg on days 4 to 6 and 1.5 mg/kg on days 7 to 9. The control animals were injected with placebo (0.9% sterile NaCl solution. In addition to the dexamethasone treatment, the experimental group received subcutaneous injections of the glucocorticoid receptor antagonist RU 38486 (Sigma, Deisenhofen, Germany) in sesame oil solution in a dose of 10 mg/kg daily according to the schedule given above.

Male sexual behavior was evaluated on the ninth day by the method given above. After the behavior test, blood samples were taken from the retroorbital plexus for determining the serum testosterone level. The testosterone was determined with a commercial test formulation (IBL, Hamburg, Germany).

Results

Chronic treatment with dexamethasone led to a significant inhibition of male sexual activity in comparison to the placebo group. Simultaneous administration of dexamethasone and the glucocorticoid receptor antagonist RU 38486 resulted in a retention of male sexual behavior at the level of the placebo group.

Daily injections of dexamethasone led to a significant reduction in the serum testosterone level in comparison to placebo treated animals. The simultaneous administration of the glucocorticoid receptor antagonist RU 38486 prevented the reduction in the serum testosterone concentration.

Conclusions

Chronic treatment with increasing doses of glucocorticoids represents a reliable pathopsysiological model of the excess activation of the glucocorticoid receptor. The pathological manifestations of this condition include the observed inhibition of male sexual behavior and the reduction in the endocrine secretory activity of the male gonads. These symptoms are also characteristic of hypogonadism and are also observed in the case of other syndromes, which are associated with an increased glucocorticoid secretion (such as Cushing Syndrome, chronic stress).

Treatment with a known antagonist of the glucocorticoid receptor prevents the inhibition of the gonadical endocrine secretion or of the male sexual activity, which are caused by dexamethasone.

TABLE 3

Effect of a chronic treatment with dexamethasone or a combination of dexamethasone and the glucocorticoid receptor antagonist RU 38486 on male sexual behavior. The data represent average values ± standard errors. The individual treatment groups consist of 13 to 15 animals; stars indicate that the differences from the placebo treatment are significant.

| Treatment Group | Male Sexual Behavior (Copulations in 5 minutes) | Serum Testosterone (ng/ml) |
|---|---|---|
| Placebo | 10.2 ± 1.3 | 17.2 ± 2.3 |
| Dexamethasone | 4.0 ± 0.9* | 2.3 ± 0.2* |
| Dexamethasone + RU38486 | 9.2 ± 1.0 | 20.2 ± 4.9 |

Example 3

Synthesis of 4-(17α-ethinyl-17β-methoxy-3-oxoestra-4,9-diene-11β-yl)benzaldehyde-1(E) oxime 4-(17α-Ethinyl-17β-methoxy-3-oxoestra-4,9-diene-11β-yl)benzaldehyde (500 mg) is reacted at room temperature under argon in 20 ml of pyridine with 103 mg of hydroxylamine hydrochloride. After four hours, the reaction mixture was stirred into 600 ml of ice water, a white product precipitating. The product is filtered off with suction and dried in air, 480 mg of a light yellow foam being obtained.

The crude product was purified by means of preparative layer chromatography with a toluene/acetone gradient. The product obtained was recrystallized from acetone, 271 mg of colorless crystals being obtained.
Melting point: 149° C. to 157° C. (acetone)
$\alpha_D$=+162° C. (Chloroform)
$^1$H-NMR(300 MHz, CDCl$_3$, TMS): 0.52 (s, 3H, H-18), 2.66 (s, 1H, C≡CH), 3.38 (s, 3H, OCH$_3$), 4.42 (d, 1H, J=7.2 Hz, H-11), 5.80 (s, 1H, H-4), 7.20 (d, 2H, J=8.2 Hz, arom. CH), 7.49 (d, 2H, J=8.4 Hz, arom. CH), 8.11 (s, 1H, CH=N), 8.39 (s, 1H, OH).
Synthesis of the Starting Compound
Step A
4-(3,3-Dimethoxy-5α,17β-dihydroxy-17α-ethinyl-estr-9-en-11β-yl)benzaldehyde-ethylene acetal 4-(3,3-Dimethoxy-5α-hydroxy-17-oxoestr-9-en-11β-yl)benzaldehyde-ethylene acetal (4.82 g) in 20 ml of THF (abs.) is cooled to −50° C. A 0.5 M solution of ethyl magnesium bromide in THF is added dropwise and the mixture is allowed to come to room temperature. After 4 hours, 100 ml of aluminum chloride solution (10%) are added dropwise with cooling, the mixture is extracted with ethyl acetate and worked up in the usual manner, 5.68 g of crude product being isolated and is purified by chromatography. A colorless foam is obtained which is processed further directly.
$\alpha_D$=−27° C. (chloroform)
$^1$H-NMR(300 MHz, CDCl$_3$, TMS): 0.42 (s, 3H, H-18), 2.58 (s, 1H, C≡CH), 3.21 and 3.22 (2s, je 3H, OCH$_3$), 4.03–4.15 (m, 4H, ethyleneketal), 4.32 (d, 1H, J=7.2Hz, H-11), 4.67 (s, 1H, OH), 5.75 (s, 1H, CH-acetal), 7.23 (d, 2H, J=8.1 Hz, arom. CH), 7.38 (d, 2H, J=8.1 Hz, arom. CH).
Step B
4-(3,3-Dimethoxy-17α-ethinyl-5α-hydroxy-17β-methoxy-estr-9-en-11α-yl)benzaldehyde ethylene acetal 4-(3,3-Dimethoxy-5α, 17β-dihydroxy-17α-ethinyl-estr-9-en-11β-yl)benzaldehyde ethylene acetal (1.01 g) in 40 ml of THF (abs.), is mixed under argon at a temperature of −38° C. consecutively with 2.2 ml of a 2.7 M butyl lithium solution in THF and subsequently with 0.86 ml of methyl iodide. The reaction mixture is allowed to come to room temperature and, after 30 hours, decomposed by the addition of water. It is extracted with ethyl acetate and worked up in the usual manner, 930 mg 4-(3,3-dimethoxy-17α-ethinyl-5α-hydroxy-17β-methoxy-estr-9-en-11β-yl)benzaldehyde ethylene acetal, being obtained as a brown foam, which is used in step C without being purified.
$^1$H-NMR(300 MHz, CDCl$_3$, TMS): 0.42 (s, 3H, H-18), 2.58 (s, 1H, C≡CH), 3.21 and 3.22 (2s, je 3H, OCH$_3$), 3.38 (s, 1H, OCH$_3$), 4.02–4.16 (m, 4H, ethyleneketal), 4.32 (d, 1H, J=7.2 Hz, H-11), 4.67 (s, 1H, OH), 5.75 (s, 1H, CH-acetal), 7.24 (d, 2H, J=8.1 Hz, arom. CH), 7.37 (d, 2H, J 8.1 Hz, arom. CH).
Step C
4-(17α-Ethinyl-17α-methoxy-3-oxoestr-4,9-diene-11β-yl)benzaldehyde 4-(3,3-Dimethoxy-17α-ethinyl-5α-hydroxy-17β-methoxy-estr-9-en-11β-yl)benzaldehyde ethylene acetal (417 mg) is dissolved in 20 ml of acetone, mixed with 2 ml water and 200 mg of p-toluenesulfonic acid and stirred for 3 hours at room temperature. By adding ice water, a crude product is precipitated, which is filtered off with suction, washed with water and dried. The crude product (300 mg) is purified by chromatography and recrystallized.
Melting point: 197° C. to 202° C. (CH$_2$Cl$_2$/acetone)
$\alpha_D$=+132° C. (Chloroform)
$^1$H-NMR (300 MHz, CDCl$_3$, TMS): 0.49 (s, 3H, H-18), 2.67 (s, 1H, C≡CH), 3.38 (s, 3H, OCH$_3$), 4.46 (d, 1H, J=7.2 Hz, H-11), 5.80 (s, 1H, H-4), 7.38 (d, 2H, J=8.1 Hz, arom. CH), 7.81 (d, 2H, J=8.4 Hz, arom. CH), 9.98 (s, 1H, CH=O).

Example 4

Synthesis of 4-(17α-ethinyl-17β-hydroxy-3-oxoestra-4,9-diene-11β-yl)benzaldehyde-1(E)-oxime The synthesis from 4-(17α-ethinyl-17β-hydroxy-3-oxoestra-4,9-diene-11β-yl)benzaldehyde is similar to that in Example 3.
Melting point: 219° C. to 221° C. (t-butyl methyl ether/n-hexane)
$\alpha_D$=+157° C. (Chloroform)
$^1$H-NMR (300 MHz, CDCl$_3$, TMS): 0.52 (s, 3H, H-18), 2.51 (s, 1H, OH), 2.65 (s, 1H, C≡CH), 4.44 (d, 1H, J=7.2 Hz, H-11), 5.80 (s, 1H, H-4), 7.20 (d, 2H, J=8.1 Hz, arom. CH), 7.59 (d, 2H, J=8.4 Hz, arom. CH), 8.11 (s, 1H, CH=N), 8.64 (s, 1H, OH).
Synthesis of the Starting Compound, 4-(17α-ethinyl-17β-hydroxy-3-oxoestra-4,9-diene-11β-yl)benzaldehyde Water (2 ml) is added to 1.2 g of 4-(3,3-dimethoxy-17α-ethinyl-5α-hydroxy-17β-methoxy-estr-9-en-11β-yl)benzaldehyde ethylene acetal in 20 ml of acetone. After the addition of 300 mg of 4-toluenesulfonic acid, the mixture is stirred for 2 hours at room temperature. The reaction solution is stirred into 300 ml of ice water, a flaky precipitate being obtained. After neutralization with sodium bicarbonate solution and stirring for 30 minutes, the precipitate is filtered off with suction, washed with water and dried under vacuum, 786 mg being obtained as a yellow foam. The crude product is purified by preparative layer chromatography on silica gel $PF_{254+366nm}$ (MERCK AG) with a mixture of 4:1 of toluene:acetone as mobile phase, 430 mg of 4-(17α-ethinyl-17β-hydroxy-3-oxoestra-4,9-diene-11β-yl) benzaldehyde being obtained. The product is recrystallized from boiling t-butyl methyl ether with addition of n-hexane. Melting point: 190° to 193° C. (t-butyl methyl ether/n-hexane)
$α_D$=+150° ($CHCl_3$)
$^1$H-NMR: [300 MHz, $CDCl_3$, TMS] (δ, ppm): 0.50 (s, 3H, H-18); 2.29 (s, 1H, OH), 2.65 (s, 1H, C≡CH), 4.49 (d, 1H, J=6.9 Hz, H-11α); 5.81 (s, 1H, H-4); 7.38 (d, 2H, J=8.1 Hz, H-2'), 7.81 (d, 2H, J=8.4 Hz, H-3'), 9.98 (s, 1H, CH=O).

Example 5

Synthesis of 4-(17β-hydroxy-17α-propinyl-3-oxoestra-4,9-diene-11β-yl)benzaldehyde-1(E)-oxime Synthesized from 4-(17β-Hydroxy-17α-propinyl-3-oxoestra-4,9-diene-11β-yl)benzaldehyde by the method of Example 3. Melting point: 149° to 151° C. (acetone / n-hexane)
$α_D$=+140° ($CHCl_3$)
$^1$H-NMR: [300 MHz, $CDCl_3$, TMS] (δ, ppm): 0.49 (s, 3H, H-18), 1.90 (s, 3H, propinyl), 4.43 (d, 1H, J=7.2 Hz, H-11α), 5.80 (s, 1H, H-4), 7.19 (d, 2H, J=8.4Hz, H-2'), 7.48 (d, 2H, J=8.4 Hz, H-3'), 8.11 (s, 1H, CH=N), 8.81 (s, 1H, NOH). HPLC: 98% F at 264 nm Example 6

Synthesis of 4-(17β-methoxy-17α-propinyl-3-oxoestra-4,9-diene-11β-yl)benzaldehyde-1(E)-oxime Synthesized from 4-(17β-Hydroxy-17α-propinyl-3-oxoestra-4,9-diene-11β-yl)benzaldehyde .
Colorless Foam
$α_D$=+143° ($CHCl_3$)
$^1$H-NMR: [300 MHz, $CDCl_3$, TMS] (δ, ppm): 0.47 (s, 3H, H-18), 1.90 (s, 3H, propinyl), 3.38 (s, 3H, $OCH_3$), 4.44 (d, 1H, J=7.2 Hz, H-11α), 5.80 (s, 1H, H-4), 7.19 (d, 2H, J=8.4 Hz, H-2'), 7.48 (d, 2H, J=8.4 Hz, H-3'), 8.11 (s, 1H, CH=N), 8.81 (s, 1H, NOH).

Example 7

Synthesis of 4-(17β-hydroxy-17α-propinyl-3-oxoestra-4,9-diene-11β-yl)benzaldehyde-1(E)-{N-[(trifluoromethoxy)phenylamino]carbonyl} oxime 4-(17≠2-Hydroxy-17α-propinyl-3-oxoestra-4,9-diene-11β-yl)benzaldehyde-1(E) oxime (725 mg) is suspended under argon in 15 ml of toluene, 0.8 ml of 4-trifluoromethoxyphenyl isocyanate are added and the mixture is stirred for 2 hours at 50° C., after which it is cooled and, after the addition of 30 ml of aqueous ammonia, extracted with dichloromethane. The organic phase is washed to neutrality, dried over sodium sulfate, filtered and concentrated under vacuum. The crude product (1.3 g) is purified by chromatography, 480 mg of 4-(17β-hydroxy-17α-propinyl-3-oxoestra-4,9-diene-11β-yl)benzaldehyde-1 (E)-{N-[(trifluoromethoxy)-phenylamino]carbonyl} oxime being obtained as a colorless foam.
$α_D$=+132° ($CHCl_3$)
$^1$H-NMR: [400 MHz, $CDCl_3$, TMS] (δ, ppm): 0.51 (s, 3H, H-18), 1.66 (s, 1H, OH), 1.92 (s, 3H, propinyl), 4.49 (d, 1H, J=7.2 Hz, H-11α), 5.81 (s, 1H, H-4), 7.22 (d, 2H, J=9.2 Hz, arom. CH), 7.29 (d, 2H, J=14.9 Hz, arom. CH), 7.56 (d, 2H, J=12.0 Hz, arom. CH), 7.65 (d, 2H, J=8.0 Hz, arom. CH), 8.19 (s, 1H, NH), 8.40 (s, 1H, CH=N).

Example 8

Synthesis of 4-[17β-hydroxy-17α,21-(phenyl)19-nor-3-oxopregna-4,9-diene-20-yn-11β-yl]benzaldehyde-1(E)-oxime Synthesis from 4-[17β-hydroxy-17α,21 -(phenyl)19-nor-3-oxopregna-4,9-diene-20-yn-11β-yl]benzaldehyde by the method of Example 3.
Synthesis of the Starting Compound
4-(3,3-Dimethoxy-5α-hydroxy-17-oxoestr-9-en-11β-yl) benzaldehyde ethylene acetal (1.93 g) is reacted with 30 ml of a 1 M phenylethinyl magnesium bromide solution in THF by the method of example 3, step A. The crude product, 4-[3,3-dimethoxy-5α, 17β-dihydroxy-17α-(phenylethinyl)-estr-9-en-11β-yl)benzaldehyde ethylene acetal (3.5 g) is purified by column chromatography on silica gel 60 (0.04–0.63 mm) with a toluene/acetone gradient and subsequently hydrolyzed with 200 mg of p-toluenesulfonic acid at room temperature in 20 ml of acetone. It is then stirred into ice water and the precipitate is filtered off with suction, washed until neutral and dried. The 4-[17β-hydroxy-17α, 21-(phenyl)19-nor-3-oxopregna-4,9-diene-20-yn-11β-yl] benzaldehyde is isolated as a colorless foam, which is used directly in the step, in which the oxime is formed.
Melting point: from 137° C. (decomposition, acetone/t-butyl methyl ether)
$α_D$=+143° ($CHCl_3$)
$^1$H-NMR: [400 MHz, $CDCl_3$, TMS] (δ, ppm): 0.57 (s, 3H, H-18), 3.38 (s, 3H, $OCH_3$), 4.45 (d, 1H, J=7.2 Hz, H-11α), 5.79 (s, 1H, H-4), 7.20 (d, 2H, J=8.0 Hz, H-2'), 7.48 (d, 2H, J=8.4 Hz, H-3'), 7.3–7.46 (m, 5H, phenyl), 8.03 (broad s, 1H, NOH), 8.11 (s, 1H, CH=N).
LC/MS: 98.8% F at $M^+$+1=492

Example 9

Synthesis of 4-[17β-hydroxy-17α,21-(4'-methylsulfonylphenyl)19-nor-3-oxopregna-4,9-diene-20-yn-11β-yl]benzaldehyde-1(E)-oxime Synthesized from 4-[17β-hydroxy-17α,21-(4'-methylsulfonylphenyl)-19-nor-3-oxopregna-4,9-diene-20-yn-11β-yl]benzaldehyde by the method of Example 3.
Melting point: from 180° C. (decomposition, dichloromethane/t-butyl methyl ether)
$α_D$=5° ($CHCl_3$)
$^1$H-NMR: [400 MHz, $CDCl_3$, TMS] (δ, ppm): 0.58 (s, 3H, H-18), 2.41 (s, 1H, OH), 3.05 (s, 3H, $SO_2CH_3$), 4.45 (broad s, 1H, H-11α), 5.79 (s, 1H, H-4), 7.20 (d, 2H, J=8.0 Hz, H-2'), 7.49 (d, 2H, J=8.0 Hz, H-3'), 7.62 (d, 1H, J=12.0 Hz, arom. CH), 7.90 (s, 2H, J=12.4 Hz, arom. CH), 5H, phenyl), 8.03 (s, 1H, NOH), 8.10 (s, 1H, CH=N).
LC/MS: 97.6% F at $M^+$+1 =570
Synthesis of Starting Compound
4-[17β-hydroxy-17α,21-(4'-methylsulfonylphenyl)19-nor-3-oxopregna-4,9-diene-20-yn-11β-yl]benzaldehyde
Palladium acetate (14.8 mg) and 34.5 mg of triphenyl phosphine were suspended under argon in 5 ml of triethylamine. After the suspension is stirred for 10 minutes, 25 mg of copper iodide and 309.2 mg of 4-bromophenylmethylsulfone are added as solids. To the greenish solution, 527 mg 4-(17α-ethinyl-17β-hydroxy-3-oxoestra-4,9-diene-11β-yl-)benzaldehyde in 20 ml of absolute THF are added slowly. At the same time, there is a color change. After 12 hours, the solution is stirred into ice water and the precipitate formed is filtered off with suction until neutral. The crude 4-[17β-hydroxy-17α,21-(4'-methylsulfonylphenyl)19-nor-3-oxopregna-4,9-diene-20-yn-11β-yl)benzaldehyde (715 mg) product is purified by preparative layer chromatography on silica gel 60 $PF_{254}$ with a mixture of toluene, ethyl acetate and butyl methyl ether.

Melting point: 235° to 237° C. (acetone)
$α_D$=−21° ($CHCl_3$)
$^1$H-NMR: [400 MHz, $CDCl_3$, TMS] (δ, ppm): 0.56 (s, 3H, H-18), 3.06 (s, 3H, $SO_2CH_3$), 4.52 (s, 1H, J=7.2 Hz, H-11α), 5.80 (s, 1H, H-4), 7.38 (d, 2H, J=8.0 Hz, H-2'), 7.63 (d, 2H, J=8.4 Hz, H-3'), 7.82 (d, 1H, J=8.8 Hz, arom. CH), 7.91 (s, 2H, J=8.4 Hz, arom. CH), 9.97 (s, 1H, CH=O).
LC/MS: 98.0% F at $M^+$+1=555
HPLC: 98% F at 262 nm Example 10

Synthesis of 4-[17β-hydroxy-17α,21 -(4'-methylsulfonylphenyl)19-nor-3-oxopregna-4,9-diene-20-yn-11β-yl]benzaldehyde-1(E)-[N-(ethylamine)carbonyl]oxime The synthesis was carried out as in Example 7 by reacting 4-[17β-hydroxy-17α,21 -(4'-methylsulfonylphenyl)19-nor-3-oxopregna-4,9-diene-20-yn-11β-yl]benzaldehyde-1(E)-[N-(ethylamino)carbonyl]oxime with ethyl isocyanate in toluene.

Melting point: 158° to 162° C. (toluene/acetone/n-hexane)
$α_D$=−2°($CHCl_3$)
$^1$H-NMR: [400 MHz, $CDCl_3$, TMS] (δ, ppm): 0.58 (s, 3H, H-18), 1.23 (t, 3H, $CH_2CH_3$), 2.51 (s, 1H, OH), 3.06 (s, 3H, $SO_2CH_3$), 3.38 (m, 2H, $CH_2CH_3$), 4.48 (d, 1H, J=4.8 Hz, H-11α), 5.79 (s, 1H, H-4), 6.23 (t, 1H, NH), 7.28 (d, 2H, J=9.2 Hz, H-2'), 7.59 (d, 2H, J=8.4 Hz, H-3'), 7.62 (d, 1H, J=8.4 Hz, arom. CH), 7.89 (s, 2H, J=8.8 Hz, arom. CH), 8.29 (s, 1H, CH=NOR).
LC/MS: 96.6% Fat $M^+$+=641

Example 11

Synthesis of 4-(17β-hydroxy-17α-propinyl-3-oxoestra-4,9-diene-11β-yl)benzaldehyde-1(E)-[S-(ethylthio)carbonyl]oxime 4-(17β-Hydroxy-17α-propinyl-3-oxoestra-4,9-diene-11β-yl)benzaldehyde-1(E)-oxime (450 mg) in 10 ml of pyridine is treated at room temperature with 1.5 ml of etiol chlorocarbonate, stirred for 2 hours and poured into ice water. The product is filtered off with suction, washed until neutral, dried and purified by chromatography. 4-(17β-Hydroxy-17α-propinyl-3-oxoestra-4,9-diene-11β-yl)benzaldehyde-1(E)-[S-(ethylthio)carbonyl]oxime (210 mg) is obtained as a colorless foam.
$α_D$=+139° ($CHCl_3$)
$^1$H-NMR: [400 MHz, $CDCl_3$, TMS] (δ, ppm): 0.50 (s, 3H, H-18), 1.23 (t, 3H, $CH_2CH_3$), 1.67 (s, 1H, OH), 1.92 (s, 3H, propinyl), 3.37 (m, 2H, $CH_2CH_3$), 4.47 (d, 1H, J=7.2 Hz, H-11α), 5.80 (s, 1H, H-4), 7.22 (d, 2H, J=8.4 Hz, arom. CH), 7.55 (d, 2H, J=8.8 Hz, arom. CH), 8.39 (s, 1H, CH=N).

Example 12

Synthesis of 4-(17β-hydroxy-17α-propinyl-3-oxoestra-4,9-diene-11β-yl)benzaldehyde-1(E)-O-acetyloxime 4-(17β-Hydroxy-17α-propinyl-3-oxoestra-4,9-diene-11β-yl)benzaldehyde-1(E)-oxime (300 mg) in 10 ml of pyridine is treated at room temperature with 1.0 ml of acetic anhydride, stirred for 2 hours and poured into ice water. The product is filtered off, washed until neutral, dried and purified by chromatography, 125 mg of 4-(17β-hydroxy-17α-propinyl-3-oxoestra-4,9-diene-11β-yl)benzaldehyde-1(E)-O-cetyl-oxime being obtained as a colorless foam.
$α_D$=+133° ($CHCl_3$)
$^1$H-NMR: [400 MHz, $CDCl_3$, TMS] (δ, ppm): 0.52 (s, 3H, H-18), 1.64 (s, 1H, OH), 1.92 (s, 3H, propinyl), 2.12 (s, 3H, $OCOCH_3$), 4.45 (d, 1H, J=7.2 Hz, H-11α), 5.80 (s, 1H, H-4), 7.21 (d, 2H, J=8.4 Hz, arom. CH), 7.56 (d, 2H, J=8.4 Hz, arom. CH), 8.38 (s, 1H, CH=N).

We claim:

1. A compound of formula (I):

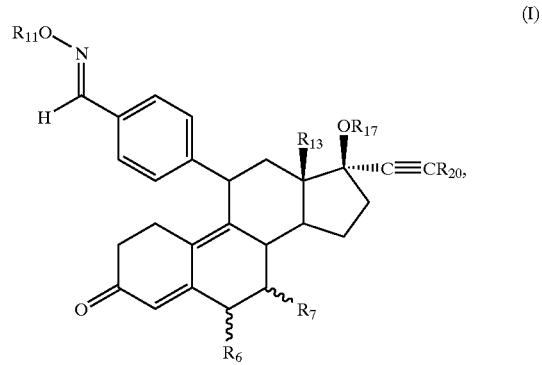

wherein $R_6$ and $R_7$ are each, independently of each other, a hydrogen atom or a halogen atom in an α or β position, or a $C_1$- to $C_6$-alkyl group in the α or β position;

$R_{11}$ is a hydrogen atom, a $C_1$- to $C_6$-alkyl group, a $C_1$- to $C_6$-acyl group, a —$CONHR_{21}$ group, a —$COSR_{22}$ group or a —$COOR_{22}$ group, in which $R_{21}$ and $R_{22}$ are each, independently of each other, a $C_1$- to $C_6$-alkyl group or an unsubstituted or substituted $C_6$- to $C_{10}$-aryl group;

$R_{13}$ is a methyl or ethyl group;

$R_{17}$ is a hydrogen atom, a $C_1$- to $C_6$-alkyl group or a $C_1$- to $C_6$-acyl group; and $R_{20}$ is a hydrogen atom, a $C_1$- to $C_6$-alkyl group or an unsubstituted or substituted $C_6$- to $C_{12}$-aryl group.

2. The compound as defined in claim 1, wherein said halogen atom is a fluorine atom, a chlorine atom or a bromine atom.

3. The compound as defined in claim 1, and consisting of an oxime compound selected from the group consisting of
4-(17α-ethinyl-17β-hydroxy-3-oxoestra-4,9-dien-11β-yl)benzaldehyde-1(E)-oxime;
4-(17α-ethinyl-17β-methoxy-3-oxoestra-4,9-dien-11β-yl)benzaldehyde-1(E)-oxime;
4-(17α-propinyl-17β-hydroxy-3-oxoestra-4,9-dien-11β-yl)benzaldehyde-1(E)-oxime;
4-(17α-propinyl-17β-methoxy-3-oxoestra-4,9-dien-11β-yl)benzaldehyde-1(E)-oxime;
4-[17β-hydroxy-17α,21-(phenyl)-19-nor-3-oxopregna-4,9-dien-20-yn-11β-yl)]-benzaldehyde-1(E)-oxime;
4-[17β-hydroxy-17α,21-(4'-methylphenyl)19-nor-3-oxopregna-4,9-dien-20-yn-11β-yl)]-benzaldehyde-1(E)-oxime;
4-[17β-hydroxy-17α,21-(t-butyl)19-nor-3-oxopregna-4,9-dien-20-yn-11β-yl)]-benzaldehyde-1(E)-oxime;
4-[17β-hydroxy-17α,21-(4'-t-butylphenyl)-19-nor-3-oxopregna-4,9-dien-20-yn-11β-yl)]-benzaldehyde-1(E)-oxime;

4-[17β-hydroxy-17α,21-(4'-methylsulfonylphenyl)-19-nor-3-oxopregna-4,9-dien-20-yn-11β-yl)]-benzaldehyde-1(E)-oxime;

4-[17β-hydroxy-17α,21-(4'-methylsulfonylphenyl)-19-nor-3-oxopregna-4,9-dien-20-yn-11β-yl)]-benzaldehyde-1(E)-[N-(ethylamine)carbonyl]oxime;

4-[17β-hydroxy-17α,21-(4'-methylsulfonylphenyl)-19-nor-3-oxopregna-4,9-dien-20-yn-11β-yl)]-benzaldehyde-1(E)-[S-(ethylthio)carbonyl]oxime;

4-[17β-hydroxy-17α,21-(4'-methylsulfonylphenyl)-19-nor-3-oxopregna-4,9-dien-20-yn-11β-yl)]-benzaldehyde-1(E)-[O-(ethyloxy)carbonyl]oxime;

4-[17β-hydroxy-17α-propinyl-13β-ethyl-3-oxopregna-4,9-dien-11β-yl)]-benzaldehyde-1(E)-oxime;

4-(6β-chloro-17β-hydroxy-17α-propinyl-3-oxoestra-4,9-dien-11β-yl)-benzaldehyde-1(E)-oxime;

4-[7α-methyl-17β-hydroxy-17α-propinyl-3-oxoestra-4,9-dien-11β-yl]-benzaldehyde-1(E)-oxime;

4-[17β-acetoxy-17α-propinyl-3-oxoestra-4,9-dien-11β-yl)]-benzaldehyde-1(E)-oxime;

4-[17β-acetoxy-17α,21-(4'-methylsulfonylphenyl)-19-nor-3-oxopregna-4,9-dien-20-yn-11β-yl)]-benzaldehyde-1(E)-O-acetyloxime; and 4-(17β-hydroxy-17α-propinyl-3-oxoestra-4,9-dien-11β-yl)benzaldehyde-1(E)-[N-(trifluoromethoxyphenylamino)carbonyl]oxime.

4. A method of synthesizing a compound of formula (I):

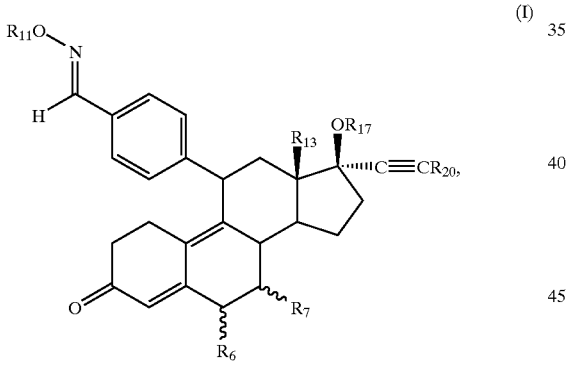

(I)

wherein $R_6$ and $R_7$ are each, independently of each other, a hydrogen atom or a halogen atom in an α or β position, or a $C_1$- to $C_6$-alkyl group in the α or β position;

$R_{11}$ is a hydrogen atom, a $C_1$- to $C_6$-alkyl group, a $C_1$- to $C_6$-acyl group, a —$CONHR_{21}$ group, a —$COSR_{22}$ group or a —$COOR_{22}$ group, in which $R_{21}$ and $R_{22}$ are each, independently of each other, a $C_1$- to $C_6$-alkyl group or an unsubstituted or substituted $C_6$- to $C_{10}$-aryl group;

$R_{13}$ is a methyl or ethyl group;

$R_{17}$ is a hydrogen atom, a $C_1$- to $C_6$-alkyl group or a $C_1$- to $C_6$-acyl group; and $R_{20}$ is a hydrogen atom, a $C_1$- to $C_6$-alkyl group or an unsubstituted or substituted $C_6$- to $C_{12}$-aryl group; said method comprising the steps of:

a) reacting an 11β-formylphenyl steroid of formula (II):

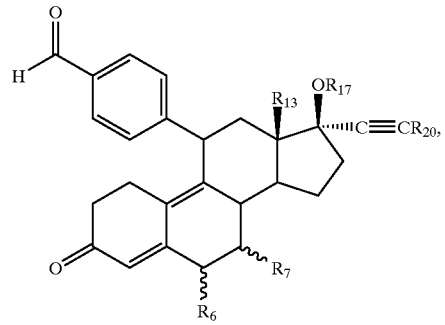

(II)

with at least one of hydroxylamine and a salt of hydroxylamine in a solvent in the presence of a base to form a corresponding 11β-benzaldoxime; and optionally b) esterifying or etherifying one or more hydroxyl groups present, or converting said hydroxyl groups into urethane groups.

5. The method as defined in claim 4, wherein said compound of formula (I) is selected from the group consisting of 4-(17α-ethinyl-17β-hydroxy-3-oxoestra-4,9-dien-11β-yl)benzaldehyde-1(E)-oxime;

4-(17α-ethinyl-17β-methoxy-3-oxoestra-4,9-dien-11β-yl)benzaldehyde-1(E)-oxime;

4-(17α-propinyl-17β-hydroxy-3-oxoestra-4,9-dien-11β-yl)benzaldehyde-1(E)-oxime;

4-(17α-propinyl-17β-methoxy-3-oxoestra-4,9-dien-11β-yl)benzaldehyde-1(E)-oxime;

4-[17β-hydroxy-17α,21-(phenyl)19-nor-3-oxopregna-4,9-dien-20-yn-11β-yl)]-benzaldehyde-1(E)-oxime;

4-[17β-hydroxy-17α,21-(4'-methylphenyl)19-nor-3-oxopregna-4,9-dien-20-yn-11β-yl)]-benzaldehyde-1(E)-oxime;

4-[17β-hydroxy-17α,21 -(t-butyl)19-nor-3-oxopregna-4,9-dien-20-yn-11β-yl)]-benzaldehyde-1(E)-oxime;

4-[17β-hydroxy-17α,21-(4'-t-butylphenyl)19-nor-3-oxopregna-4,9-dien-20-yn-11β-yl)]-benzaldehyde-1(E)-oxime;

4-[17β-hydroxy-17α,21 -(4'-methylsulfonylphenyl)19-nor-3-oxopregna-4,9-dien-20-yn-11β-yl)]-benzaldehyde-1(E)-oxime;

4-[17β-hydroxy-17α,21 -(4'-methylsulfonylphenyl)19-nor-3-oxopregna-4,9-dien-20-yn-11β-yl)]-benzaldehyde-1(E)-[N-(ethylamine)carbonyl]oxime;

4-[17β-hydroxy-17α,21 -(4'-methylsulfonylphenyl)19-nor-3-oxopregna-4,9-dien-20-yn-11β-yl)]-benzaldehyde-1(E)-[S-(ethylthio)carbonyl]oxime;

4-[17β-hydroxy-17α,21 -(4'-methylsulfonylphenyl)19-nor-3-oxopregna-4,9-dien-20-yn-11β-yl)]-benzaldehyde-1(E)-[O-(ethyloxy)carbonyl]oxime;

4-[17β-hydroxy-17α-propinyl-13β-ethyl-3-oxoestra-4,9-dien-11β-yl)]-benzaldehyde-1(E)-oxime;

4-(6β-chloro-17β-hydroxy-17α-propinyl-3-oxoestra-4,9-dien-11β-yl)-benzaldehyde-1(E)-oxime;

4-[7α-methyl-17β-hydroxy-17α-propinyl-3-oxoestra-4,9-dien-11β-yl]-benzaldehyde-1(E)-oxime;

4-[17β-acetoxy-17α-propinyl-3-oxoestra-4,9-dien-11β-yl)]-benzaldehyde-1(E)-oxime;

4-[17β-acetoxy-17α,21 -(4α-methylsulfonylphenyl)-19-nor-3-oxopregna-4,9-dien-20-yn-11β-yl)]-benzaldehyde-1(E)-O-acetyloxime; and 4-(17β-hydroxy-17α-propinyl-3-oxoestra-4,9-dien-11β-yl)benzaldehyde-1(E)-[N-(trifluoromethoxyphenylamino)carbonyl]oxime.

6. A method of treating or preventing a disease in a human male or a male animal caused by a decreased production of androgens in said human male or said male animal, said method comprising the step of administering an effective amount of a glucocorticoid receptor antagonist to said human male or said male animal in order to increase production of the androgens.

7. The method as defined in claim 6, wherein said glucocorticoid receptor antagonist is administered to said human male and said disease is hypogonadism, sexual dysfunction or infertility.

8. The method as defined in claim 6, wherein said glucocorticoid receptor antagonist antagonizes type 1 transcription induction of a glucocorticoid receptor gene.

9. The method as defined in claim 6, wherein said glucocorticoid receptor antagonist essentially does not antagonize type 2 transcription inhibition.

10. The method as defined in claim 6, wherein said glucocorticoid receptor antagonist essentially does not bind to any other steroid receptors.

11. The method as defined in claim 6, wherein said glucocorticoid receptor antagonist essentially incompletely inhibits signals, mediated by glucocorticoid receptors.

12. The method as defined in claim 6, wherein said androgens include testosterone.

13. The method as defined in claim 6, wherein said glucocorticoid receptor antagonist is selected from the group consisting of 4-(17α-ethinyl-17β-hydroxy-3-oxoestra-4,9-dien-11β-yl)benzaldehyde-1(E)-oxime;

4-(17α-ethinyl-17β-methoxy-3-oxoestra-4,9-dien-11β-yl)benzaldehyde-1(E)-oxime;

4-(17α-propinyl-17β-hydroxy-3-oxoestra-4,9-dien-11β-yl)benzaldehyde-1(E)-oxime;

4-(17α-propinyl-17β-methoxy-3-oxoestra-4,9-dien-11β-yl)benzaldehyde-1(E)-oxime;

4-[17β-hydroxy-17α,21-(phenyl)19-nor-3-oxopregna-4,9-dien-20-yn-11β-yl)]-benzaldehyde-1(E)-oxime;

4-[17β-hydroxy-17α,21-(4'-methylphenyl)19-nor-3-oxopregna-4,9-dien-20-yn-11β-yl)]-benzaldehyde-1(E)-oxime;

4-[17β-hydroxy-17α,21 -(t-butyl)19-nor-3-oxopregna-4,9-dien-20-yn-11β-yl)]-benzaldehyde-1(E)-oxime;

4-[17β-hydroxy-17α,21 -(4'-t-butylphenyl)19-nor-3-oxopregna-4,9-dien-20-yn-11β-yl)]-benzaldehyde-1(E)-oxime;

4-[17β-hydroxy-17α,21 -(4'-methylsulfonylphenyl)19-nor-3-oxopregna-4,9-dien-20-yn-11β-yl)]-benzaldehyde-1(E)-oxime;

4-[17β-hydroxy-17α,21 -(4'-methylsulfonylphenyl)19-nor-3-oxopregna-4,9-dien-20-yn-11β-yl)]-benzaldehyde-1(E)-[N-(ethylamine)carbonyl]oxime;

4-[17β-hydroxy-17α,21 -(4'-methylsulfonylphenyl)19-nor-3-oxopregna-4,9-dien-20-yn-11β-yl)]-benzaldehyde-1(E)-[S-(ethylthio)carbonyl]oxime;

4-[17β-hydroxy-17α,21 -(4'-methylsulfonylphenyl)19-nor-3-oxopregna-4,9-dien-20-yn-11β-yl)]-benzaldehyde-1(E)-[O-(ethyloxy)carbonyl]oxime;

4-[17β-hydroxy-17α-propinyl-13β-ethyl-3-oxoestra-4,9-dien-11β-yl)]-benzaldehyde-1(E)-oxime;

4-(6β-chloro-17β-hydroxy-17α-propinyl-3-oxoestra-4,9-dien-11β-yl)-benzaldehyde-1(E)-oxime;

4-[7α-methyl-17β-hydroxy-17α-propinyl-3-oxoestra-4,9-dien-11β-yl]-benzaldehyde-1(E)-oxime;

4-[17β-acetoxy-17α-propinyl-3-oxoestra-4,9-dien-11β-yl)]-benzaldehyde-1(E)-oxime;

4-[17β-acetoxy-17α,21-(4'-methylsulfonylphenyl)-19-nor-3-oxopregna-4,9-dien-20-yn-11β-yl)]-benzaldehyde-1(E)-O-acetyloxime; and 4-(17β-hydroxy-17α-propinyl-3-oxoestra-4,9-dien-11β-yl)benzaldehyde-1(E)-[N-(trifluoromethoxyphenylamino)carbonyl]oxime.

14. A pharmaceutical composition for treating a disease of a human male caused by an androgen deficiency, said pharmaceutical composition containing at least one of pharmaceutically acceptable adjuvants and carriers together with an effective amount of a glucocorticod receptor antagonist.

15. The pharmaceutical composition as defined in claim 14, wherein said effective amount is from 0.0001 to 100 mg of said glucocorticod receptor antagonist per kg of weight of said human male.

16. The pharmaceutical composition as defined in claim 14, wherein said glucocorticoid receptor antagonist is selected from the group consisting of 4-(17α-ethinyl-17β-hydroxy-3-oxoestra-4,9-dien-11β-yl)benzaldehyde-1(E)-oxime;

4-(17α-ethinyl-17β-methoxy-3-oxoestra-4,9-dien-11β-yl)benzaldehyde-1(E)-oxime;

4-(17α-propinyl-17β-hydroxy-3-oxoestra-4,9-dien-11β-yl)benzaldehyde-1(E)-oxime;

4-(17α-propinyl-17β-methoxy-3-oxoestra-4,9-dien-11β-yl)benzaldehyde-1(E)-oxime;

4-[17β-hydroxy-17α,21-(phenyl)19-nor-3-oxopregna-4,9-dien-20-yn-11β-yl)]-benzaldehyde-1(E)-oxime;

4-[17β-hydroxy-17α,21-(4'-methylphenyl)19-nor-3-oxopregna-4,9-dien-20-yn-11β-yl)]-benzaldehyde-1(E)-oxime;

4-[17β-hydroxy-17α,21-(t-butyl)19-nor-3-oxopregna-4,9-dien-20-yn-11β-yl)]-benzaldehyde-1(E)-oxime;

4-[17β-hydroxy-17α,21-(4'-t-butylphenyl)19-nor-3-oxopregna-4,9-dien-20-yn-11β-yl)]-benzaldehyde-1(E)-oxime;

4-[17β-hydroxy-17α,21-(4'-methylsulfonylphenyl)19-nor-3-oxopregna-4,9-dien-20-yn-11β-yl)]-benzaldehyde-1(E)-oxime;

4-[17β-hydroxy-17α,21-(4'-methylsulfonylphenyl)19-nor-3-oxopregna-4,9-dien-20-yn-11β-yl)]-benzaldehyde-1(E)-[N-(ethylamine)carbonyl]oxime;

4-[17β-hydroxy-17α,21-(4'-methylsulfonylphenyl)19-nor-3-oxopregna-4,9-dien-20-yn-11β-yl)]-benzaldehyde-1(E)-[S-(ethylthio)carbonyl]oxime;

4-[17β-hydroxy-17α,21 -(4'-methylsulfonylphenyl)19-nor-3-oxopregna-4,9-dien-20-yn-11β-yl)]-benzaldehyde-1(E)-[O-(ethyloxy)carbonyl]oxime;

4-[17β-hydroxy-17α-propinyl-13β-ethyl-3-oxoestra-4,9-dien-11β-yl)]-benzaldehyde-1(E)-oxime;

4-(6β-chloro-17β-hydroxy-17α-propinyl-3-oxoestra-4,9-dien-11β-yl)-benzaldehyde-1(E)-oxime;

4-[7α-methyl-17β-hydroxy-17α-propinyl-3-oxoestra-4,9-dien-11β-yl]-benzaldehyde-1(E)-oxime;

4-[17β-acetoxy-17α-propinyl-3-oxoestra-4,9-dien-11β-yl)]-benzaldehyde-1(E)-oxime;

4-[17β-acetoxy-17α,21 -(4'-methylsulfonylphenyl)-19-nor-3-oxopregna-4,9-dien-20-yn-11β-yl)]-benzaldehyde-1(E)-O-acetyloxime; and 4-(17β-hydroxy-17α-propinyl-3-oxoestra-4,9-dien-11β-yl)benzaldehyde-1(E)-[N-(trifluoromethoxyphenylamino)carbonyl]oxime.

* * * * *